(12) United States Patent
Iversen et al.

(10) Patent No.: US 7,094,765 B1
(45) Date of Patent: Aug. 22, 2006

(54) ANTISENSE RESTENOSIS COMPOSITION AND METHOD

(75) Inventors: Patrick L. Iversen, Corvallis, OR (US); Dwight D. Weller, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 0 days.

(21) Appl. No.: 09/493,427

(22) Filed: Jan. 29, 2000

Related U.S. Application Data

(60) Provisional application No. 60/117,846, filed on Jan. 29, 1999.

(51) Int. Cl.
- *A01N 43/04* (2006.01)
- *A61K 31/07* (2006.01)
- *C12N 5/00* (2006.01)
- *C07H 21/04* (2006.01)

(52) U.S. Cl. ............................. 514/44; 435/6; 435/325; 435/375; 536/24.5

(58) Field of Classification Search .................. 514/44; 435/6, 325, 375; 536/23.1, 24.5, 24.3, 24.33
See application file for complete search history.

(56) References Cited

U.S. PATENT DOCUMENTS

| | | | |
|---|---|---|---|
| 5,378,841 A | * | 1/1995 | Summerton et al. ........ 544/118 |
| 5,756,476 A | | 5/1998 | Epstein et al. |
| 5,871,535 A | * | 2/1999 | Wolff et al. |
| 5,912,332 A | * | 6/1999 | Agrawal et al. ........... 536/23.1 |
| 5,997,468 A | * | 12/1999 | Wolff et al. |
| 6,133,242 A | * | 10/2000 | Zalewski et al. ............. 514/44 |
| 6,159,946 A | * | 12/2000 | Zalewski et al. ............. 514/44 |

FOREIGN PATENT DOCUMENTS

WO    WO 9846740 A1 * 10/1998

OTHER PUBLICATIONS

Kobayashi et al. Growth inhibition of gastrointestinal cancer by antisense oligonucleotides. Osaka Daigaku Zasshi, vol. 47, No. 6-12, abstract. 1995.*
Kutryk, M. et al., "Local Intracoronary Administration of Antisense Oligonucleotide Against c-*myc* for the Prevention of In-Stent Restenosis", *Journal of the American College of Cardiology* 39(2):281-287, 2002.
Bult, Hidde, "Restenosis: a challenge for pharmacology", *TIPS* 21:274-279, 2000.
Kent, K. and Liu, B., "Intimal Hyperplasia—Still Here after All These Years!", *Annals of Vascular Surgery, Inc.* 18(2):135-137, 2004.
Roqué, F. et al., "Safety of Intracoronary Administration of c-*myc* Antisense Oligomers After Percutaneous Transluminal Coronary Angioplasty (PTCA)", *Antisense & Nucleic Acid Drug Development* 11:99-106, 2001.
Gruberg, L. et al., "Novel approaches for the prevention of restenosis", *Exp. Opin. Invest. Drugs* 9(11):2555-2578, 2000.

* cited by examiner

*Primary Examiner*—Janet L. Epps-Ford
(74) *Attorney, Agent, or Firm*—Perkins Coie LLP

(57) ABSTRACT

The present invention provides an improved method for reducing the risk or severity of restenosis following cardiac angioplasty. The method includes administering to a target vessel region, a morpholino antisense compound having uncharged phosphorus-containing backbone linkages, and spanning the start codon of a human c-myc mRNA. Also disclosed are novel antisense compounds and compositions, and a method for assaying the effectiveness of antisense delivery and uptake to a target vessel region.

13 Claims, 3 Drawing Sheets

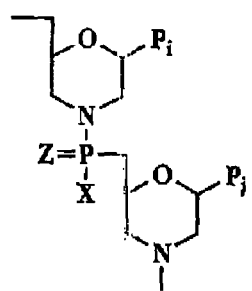
Fig. 2A-A
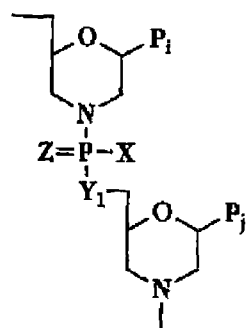
Fig. 2B-B
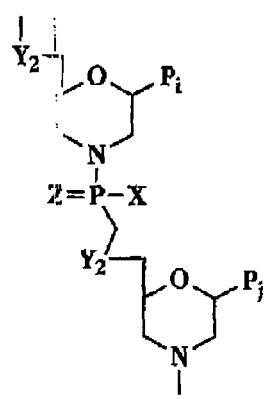
Fig. 2C-C
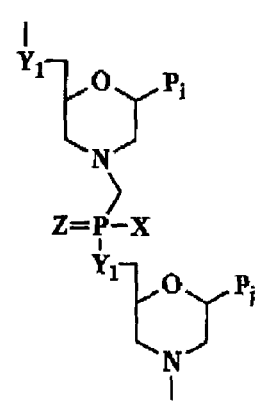
Fig. 2D-D/E-E

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence

```
-continued

<220> FEATURE:
<223> OTHER INFORMATION: antisense

<400> SEQUENCE: 1
acgttgaggg gcatcgtcgc                                              20
```

ANTISENSE RESTENOSIS COMPOSITION AND METHOD

This application claims priority to U.S. provisional application for "Non-invasive Method for Detecting Target RNA", Ser. No. 60/117,846, filed Jan. 29, 1999, which is incorporated by reference into the present application.

FIELD OF THE INVENTION

The present invention relates to compositions and methods for treating restenosis, and in particular to an antisense composition directed against c-myc, and a method of administering the composition to reduce the risk of restenosis in transluminal angioplasty, such as percutaneous transluminal coronary angioplasty (PTCA).

REFERENCES

Alfke H; et al.; *Cardiovasc Intervent Radiol*, January–February 1998, 21 (1) p. 50–6.
Allen R T; et al.; *Scanning*, November 1998, 20 (8) p. 577–86.
Badimon L; et al.; *Z Kardiol*, 1995; 84 Suppl 4 p. 145–9.
Barath P; et al.; *Cathet Cardiovasc Diagn*, July 1997, 41 (3) p. 333–41.
Bartorelli A L; et al. *Cathet Cardiovasc Diag*, November 1997, 42 (3) p. 313–20.
Bauriedel G; et al., *Z Kardiol*, 1994, 83 Suppl 4 p. 31–41.
Ben-Yosef, T., et al., *Oncogene* 17(2):165–71, 1998.
Bennett M R; et al., *Biochem J*, Sep. 15 1994, 302 (Pt 3) p. 701–8.
Bennett M R; et al., *J Clin Invest*, February 1994, 93 (2) p. 820–8.
Burgess T L; et al., *Proc Natl Acad Sci USA*, April 25 1995, 92 (9) p. 4051–5.
Casterella P J; et al., *Cardiol Rev*, July–August 1999, 7 (4) p. 219–31.
Chen S J; et al., *Circulation*, November 1994, 90 (5) p. 2468–73.
Consigny P M; et al., *J Vasc Interv Radiol*, September–October 1994, 5 (5) p. 731–7.
Dev N B; et al., *Cathet Cardiovasc Diagn*, November 1998, 45 (3) p. 337–45.
Dick A; et al., *Cardiovasc Intervent Radiol*, September–October 1999, 22 (5) p. 389–93.
Fernandez-Ortiz A; et al., *Circulation*, Apr. 1994, 89 (4) p. 1518–22.
Gottman D; et al., *Rofo Fortschr Geb Rontgenstr Neuen Bildgeb Verfahr*, January 1999, 170 (1) p. 84–8.
Hamon M; et al., *Drugs Aging*, October 1998, 13 (4) p. 291–301.
Herdeg C; et al., *Cathet Cardiovasc Diagn*, Jul. 1997, 41 (3) p. 308–14.
Hodgkin D D; et al., *J Cardiovasc Pharmacol*, January 1997, 29 (1) p. 39–44.
Hong M K; et al., *Cathet Cardiovasc Diagn*, March 1995, 34 (3) p. 263–70.
Hong M K; et al., *Coron Artery Dis*, November 1993, 4 (11) p. 1023–7.
Imanishi T et al., *Jpn. Circ. J.*, 61(3) 256–262, 1997.
Kimura T; et al., *Jpn Circ J*, April 1998, 62 (4) p. 299–304.
Koh W J; et al., *Int J Radiat Oncol Biol Phys.*, Nov. 1 1996, 36 (4) p. 829–34.
Lambert C R; et al., *Coron Artery Dis*, May 1993, 4 (5) p. 469–75.
Lee M; et al., *Antisense Nucleic Acid*, Drug Dev October 1999, 9 (5); p. 487–92.
Meyer B J; et al., *Circulation*, November 1994, 90 (5) p2474–80.
Oberhoff M; et al., *Cathet Cardiovasc Diagn*, July 1997, 41 (3) p268–74.
Pavlides G S; et al., *Cathet Cardiovasc Diagn*, July 1997, 41 (3) p287–92.
Porter T R; et al., *J Ultrasound Med*, August 1996, 15(8): 577.
Raman V K; et al., *Semin Interv Cardiol*, September–December 1998, 3 (3–4) p133–7.
Robinson K A; et al., *Cathet Cardiovasc Diagn*, July 1997, 41 (3) p354–9.
Robinson K A; et al., *Cathet Cardiovasc Diagn*, July 1997, 41 (3) p348–53.
Roy S; et al., *J Vasc Interv Radiol* June 1999, 10 (6) p817–24.
Rubartelli P; et al., *J Am Coll Cardiol*, July 1998, 32 (1) p90–6.
Savage M P; et al., *J Am Coll Cardiol*, February 1998, 31 (2) p307–11.
Sirnes P A; et al., *Int J Cardiol*, Dec. 1 1998, 67(2) p. 111–8.
Skaletz-Rorowski A; et al., *Arterioscler Thromb Vasc Biol*, July 1999; 19(7) p. 1608–14.
Teomim D; et al., *J Controlled Releas*, Jun. 28 1999, 60 (1) p129–42.
Wilensky R L; et al., *Am Heart J* October 1991, 122 (4 Pt 1) p1136–40.

BACKGROUND OF THE INVENTION

Transluminal coronary angioplasty was introduced in the late 1970's as a nonsurgical treatment for obstructive coronary artery disease. Since its introduction, major advances in equipment and techniques have led to widespread use of the method for treating coronary artery disease and angina. Typically, the procedure involves placing a balloon-tip catheter at the site of occlusion, and disrupting and expanding the occluded vessel by inflating the catheter balloon.

Despite improvements in equipment and techniques, restenosis persists as the limiting factor in the maintenance of vessel patency in angioplasty, occurring in 30% to 50% of patients, and accounting for significant morbidity and health care expenditures. (Casterella). Post-angioplasty restenosis is a segmentally limited, wound healing response to a traumatization of the vascular wall. Studies with animal models and human autopsy plaque tissue indicate a cascade-like course of events triggered by (a) destruction of endothelial and subendothelial structures, (b) traumatization of medial regions with rupture of the internal elastic lamina, (c) release of thrombogenic factors such as collagen or tissue factor, (d) stretching of smooth muscle cells with subsequent expression of proto-oncogenes (c-fos, c-myc, c-myb), (e) release of growth factors from cells of the bloodstream, endothelial cells and SMCs, and (f) thrombin production with autocatalytic activation of the SMC thrombin receptor (Bauriedel).

Overlapping the inflammation period, granulation begins 3 days after angioplasty. Proteinases such as plasmin as well as collagenases induce the disintegration of extracellular matrix structures, thereby modulating plaque formation, and lead to an organelle-rich SMC phenotype within the intima and media. Overlapping with the granulation period, induction of different components of the extracellular matrix occurs 1–2 weeks after angioplasty, possibly mediated by TGF-beta (phase of matrix formation). Smooth muscle cells produce and secrete matrix proteins such as tenascin, fibronectin, collagens and proteoglycans, and thereby induce a marked increase of the neointimal plaque volume. (Bauriedel).

Clinical trials in restenosis prevention using various revascularization devices, antiplatelet drugs, antithrombotic drugs, and anti-inflammatory agents have produced limited improvement in the incidence of restenosis. Also reported are attempts to improve the risk or severity of restenosis with intravascular stents (Savage, Eisenhower, Rubarteli, Gottman), radiation therapy (Koh), and administration of anti-proliferative drugs at the vessel injury site. The latter approach typically employs the balloon catheter for introducing the therapeutic agent at the vessel occlusion site (Dick, Roy, Dev, Kimura, Alfke, Robinson 1997a, Robinson 1997b, Barath, Herdeg, Pavlides, Oberhoff, Hodgkin, Hong, Consigny, Meyer, Fernadez-Ortiz, Lambert, and Wilensky), or releasing drug from a stent (Teomin, Bartonelli, Raman, Gibson).

Despite these advances, the incidence of restenosis, and the inability to predict the response to treatment, remains a serious risk factor in vascular angioplasty. It would therefore be desirable to (i) provide a treatment method which shows efficacy in reducing the incidence and severity of restenosis following vascular angioplasty, (ii) is well tolerated by the patients, with few or any side effects, and (iii) can be carried out with a variety of therapeutic delivery methods.

It would also be desirable to provide improved therapeutic compounds and compositions for carrying out the method, and a simple, rapid clinical assay for monitoring effectiveness of the delivery of a therapeutic compound to the vessel target site.

SUMMARY OF THE INVENTION

In one aspect, the invention includes a method of reducing the risk of restenosis in a region of a patient's coronary vessel which has been treated by coronary angioplasty using a catheter with a distal-end expandable balloon, or which is at a vessel junction formed in a coronary bypass operation. The method includes administering to the patient, by direct local administration to the vessel site or injury, a morpholino antisense compound having (i) from 8 to 40 nucleotides, including a targeting base sequence that is complementary to a region that spans the translational start codon of a c-myc mRNA, and (ii) uncharged, phosphorous-containing intersubunit linkages, in an amount effective to reduce the risk or severity of restenosis in the patient.

The administering is carried out by (a) contacting the region of the vessel with a reservoir containing the antisense compound, and introducing the compound from the reservoir into the vessel by iontophoresis or electroporation; (b) injecting the compound from the catheter directly into the region of the vessel, under pressure, through injectors contained on the surface of the catheter balloon, where the injectors are capable of penetrating the tunica media in the vessel; (c) injecting into or placing at the region of the vessel, microparticles containing the antisense compound in entrapped form; (d) contacting the region of the vessel with a hydrogel coating contained on the surface of the catheter balloon, and containing the antisense compound in diffusable form; or (e) contacting the region of the vessel with a stent having an outer surface layer containing the antisense compound in diffusable form.

The antisense compound preferably has intersubunit linkages selected from the group consisting of the structures presented in FIGS. 2AA–2EE, and exemplified particularly by the phosphorodiamidate linkage represented at FIGS. 2B-B, where $X=NH_2$, $Y=O$, and $Z=O$. An exemplary sequence is the one identified by SEQ ID NO:1.

For use in mode of administration (a), the antisense compound is preferably contained in a volume between two inflated balloons in the catheter, and the volume is subjected to pulsed electric fields effective to ionotophoretically drive the compound into region of the vessel.

For use in mode of administration (b), the catheter balloon preferably has a plurality of outer-facing channels that communicate with a distal-tip reservoir, where each channel having one or more injection ports or fingers, and the injecting step includes forcing a solution or suspension of the antisense compound from the reservoir through the injection ports when the balloon is in an inflated position.

For use in mode of administration (c), the catheter preferably has a distal end reservoir, the microparticles are contained as a particle suspension in the reservoir, and the injecting step includes forcing the suspension out of the catheter through a catheter surface in contact with the vessel region. Exemplary particles include biodegradable polymer particles or liposomes with entrapped antisense compounds or microbubbles designed to release entrapped compound when subjected to ultrasonic energy.

For use in mode of mode of administration (d), the hydrogel coating is preferably designed to release the majority of the antisense compound in the coating over a period of 5–60 minutes following balloon angioplasty.

For use in mode (e), the stent may be biodegradable, and designed to release the majority of the antisense compound in the coating over a period of 5–60 minutes following balloon angioplasty.

In a related aspect, the invention includes a method of reducing the risk of restenosis in a region of a patient's coronary vessel that has been treated by coronary angioplasty using a catheter with a distal-end expandable balloon. The method includes administering to the patient, by direct administration to the site of injury, a morpholino antisense compound having (i) the base sequence identified as SEQ ID NO:1, and (ii) a phosphorodiamidate backbone shown in. FIGS. 2B-B, where $X=NH_2$, $Y=O$, and $Z=O$. The antisense compound may be derivatized, e.g., at its 5' end, with a moiety that enhances the solubility of the compound in aqueous medium, and/or with a moiety that imparts a charge to the compound at physiological pH. The compound is preferably delivered by direct application of the compound to the target vessel region, immediately following balloon angioplasty, or during a coronary bypass operation, in an amount of between about 1–30 mg, to achieve a final amount of compound administered to the target region of between about 0.5 to 2 mg.

In another aspect, the invention includes a morpholino antisense compound having (i) from 8 to 40 nucleotides, including a targeting nucleic acid sequence complementary to a region that spans the start codon of a human c-myc mRNA gene, and (ii) uncharged, phosphorous-containing intersubunit linkages. The intersubunit linkages are preferably selected from the group consisting of the structures presented in FIGS. 2A-A–2E-E, as exemplified particularly by the phosphorodiamidate linkage represented at FIGS. 2B-B, where $X=NH_2$, $Y=O$, and $Z=O$. An exemplified sequence is given by the sequence identified by SEQ ID NO:1. The antisense compound may be derivatized, e.g., at its 5' end, with a moiety that enhances the solubility of the compound in aqueous medium, and/or with a moiety that imparts a charge to the compound at physiological pH. The compound may be included in a liposomal or other microparticle vehicle.

In still another aspect, the invention includes a method for assaying the ability of an antisense compound to reach and interact with c-myc mRNA in vessel cells, in a treatment method using antisense compound to reduce the risk of restenosis. The method includes (a) administering to the patient, a morpholino antisense compound having a substantially uncharged backbone, and a sequence that spans the start codon of a human c-myc mRNA, (b) at a selected time after the compound is administered, taking a sample of a body fluid from the subject, and (c) detecting in the sample, the presence of a nuclease-resistant heteroduplex composed of the antisense compound and the target RNA region.

These and other objects and features of the present invention will become more fully apparent when the following detailed description of the invention is read in conjunction with the accompanying drawings.

BRIEF DESCRIPTION OF THE DRAWINGS

FIGS. 2A-A to 2E-E show the repeating subunit segment of exemplary morpholino oligonucleotides, designated A—A through E—E, constructed using subunits A–E, respectively, of FIG. 1.

DETAILED DESCRIPTION OF THE INVENTION

I. Definitions

Figure 1A:
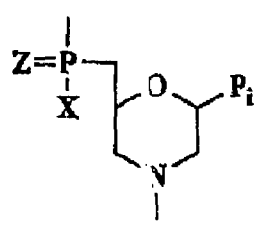
FIG. 1 shows several preferred subunits having 5-atom (A), six-atom (B) and seven-atom (C–E) linking groups suitable for forming polymers.
Figure 1B:
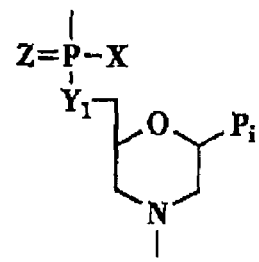
Figure 1C:
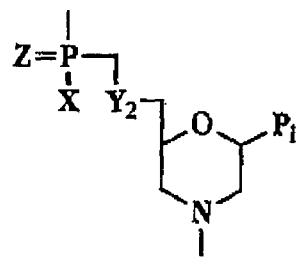
Figure 1D:
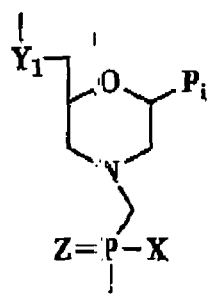
Figure 1E:
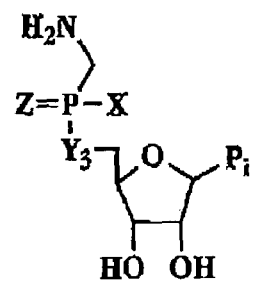

The terms below, as used herein, have the following meanings, unless indicated otherwise:

"Antisense" refers to an oligomer having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence, typically with an mRNA. The oligomer may have exact sequence complementarity to the target sequence or near complementarity. These antisense oligomers may block or inhibit translation of the mRNA, and/or modify the processing of an mRNA to produce a splice variant of the mRNA. Studies conducted in support of the present invention, for example, show that the antisense compound represented by SEQ ID NO:1 interferes with c-myc mRNA processing, leading to a truncated mRNA in which the normal start codon and adjacent region has been spliced out of the mRNA.

As used herein, the terms "compound", "agent", "oligomer" and "oligonucleotide" may be used interchangeably with respect to the antisense oligonucleotides of the invention. As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIGS. 2B-B, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. Exemplary structures for antisense oligonucleotides for use in the invention include the morpholino subunit types shown in FIGS. 1A–E, with the linkages shown in FIGS. 2A-A to 2E-E.

As used herein, a "nuclease-resistant" oligomeric molecule (oligomer) is one whose backbone is not susceptible to nuclease cleavage of a phosphodiester bond.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 60° C.–80° C. or higher. Such hybridization preferably corresponds to stringent hybridization conditions, selected to be about 10° C., and preferably about 50° C. lower than the thermal melting point (T[m]) for the specific sequence at a defined ionic strength and pH. At a given ionic strength and pH, the T[m] is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein, the term "c-myc antisense compound" refers to a nuclease-resistant antisense morpholino compound having high affinity (i.e., "specifically hybridizes") to a complementary or near-complementary c-myc nucleic acid sequence, e.g., the sequence including and spanning the normal AUG start site.

As used herein the term "analog" in reference to an oligomer means a substance possessing both structural and chemical properties similar to those of the reference oligomer.

As used herein, "effective amount" relative to an antisense oligomer refers to the amount of antisense oligomer administered to a mammalian subject, either as a single dose or as part of a series of doses, that is effective to reduce the risk (incidence) or severity (amount of occlusion) of restenosis, following balloon angioplasty.

As used herein, the term "body fluid" encompasses a variety of sample types obtained from a subject including, urine, saliva, plasma, blood, spinal fluid, and other liquid sample of biological origin, and may refer include cells or cell fragments suspended therein, or the liquid medium and its solutes.

II. Compound and Composition

A. c-myc Antisense Compound c-myc is a proto-oncogene which regulates cell growth and differentiation, is involved in the process of vascular remodeling, regulating smooth muscle cell proliferation and extracellular matrix synthesis, in addition to playing a role in apoptosis. Aberrant expression of c-myc is frequently observed in human cancer. Aberrant, constitutive or overexpression of c-myc has been associated with a number of human cancers including lung cancer, colorectal cancer, breast cancer, bladder cancer, leukemia, lung cancer, etc.

Several in vitro studies have demonstrated that phosphorothioate oligodeoxynucleotides targeted against genes involved in smooth muscle cell proliferation inhibit both proliferation and migration. In one study in vivo administration of phosphorothioate oligonucleotides targeted against c-myc using a porous balloon catheter in a porcine coronary artery model (Shi), and in another study phosphorothioate oligonucleotides delivered intraluminally and targeted against c-myb, c-myc, cdc2 kinase, cdk2 kinase and proliferating cell nuclear antigen (PCNA) inhibited neointimal formation after balloon injury in both the rat carotid and porcine coronary artery models (Lee).

However, a similar study single endoluminal transcatheter delivery of antisense oligonucleotides directed against cell cycle regulatory proteins using a porous balloon catheter did not affect neointima formation or vessel size (Robinson). The results of a further study using phosphorothioate oligonucleotides directed toward c-myb and c-myc indicated inhibition of smooth muscle cell proliferation. However, the observed inhibition was clearly not via an antisense mechanism, but was correlated with the presence of four contiguous guanosine residues in the oligonucleotide sequence in vitro in primary cultures of smooth muscle cells and in arteries ex vivo (Burgess).

In accordance with the present invention, it has been discovered that a morpholino antisense compound having (i) from 8 to 40 nucleotides, including a targeting base sequence that is complementary to a region that spans the translational start codon of a c-myc mRNA and (ii) uncharged, phosphorous-containing intersubunit linkages produces a significant reduction in the incidence and severity of restenosis. In vitro and animal-model studies conducted in support of the invention indicate that the antisense compound (i) is taken up efficiently by cells in a vessel lumen which are exposed to the antisense compound, (ii) acts intracellularly to inhibit correct processing (mRNA splicing) and translation of processed c-myc mRNA, and (iii) is significantly more effective, in reducing the incidence and severity of restenosis, than other types of c-myc antisense compounds, e.g., phosphorothioate c-myc antisense compounds.

The synthesis, structures, and binding characteristics of morpholino oligomers are detailed in above-cited U.S. Pat. Nos. 5,698,685, 5,217,866, 5,142,047, 5,034,506, 5,166,315, 5,521,063, and 5,506,337, all of which are incorporated herein by reference. The antisense oligomers (compounds) of the present invention are composed of morpholino subunits of the form shown in the above cited patents, where (i) the morpholino groups are linked together by uncharged phosphorus-containing linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton and Weller, 1993), which is hereby incorporated by reference in its entirety. As shown in the reference, several types of nonionic linkages may be used to construct a morpholino backbone. One such linkage is of the form:

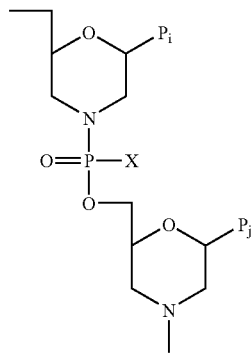

where $P_j$ is a purine or pyrimidine base-pairing moiety effective to bind by base-specific hydrogen bonding to a base in a polynucleotide; X is F, $CH_2R$, $OCH_2R$, $SCH_2R$, or $NR^1R^2$; and each of R, $R^1$ and $R^2$ is H, $CH_3$, or other moiety that does not interfere with said base specific hydrogen bonding. A further such linkage is of the form:

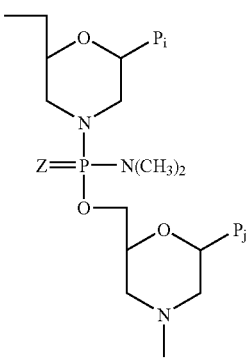

where $P_j$ is a purine or pyrimidine base-pairing moiety effective to bind by base-specific hydrogen bonding to a base in a polynucleotide; and Z is O or S.

Exemplary backbone structures for antisense oligonucleotides of the invention include the β-morpholino subunit types shown in FIGS. 1A–E. It will be appreciated that a polynucleotide may contain more than one linkage type.

Subunit A in FIG. 1 contains a 1-atom phosphorous-containing linkage which forms the five atom repeating-unit backbone shown at A—A in FIG. 2, where the morpholino rings are linked by a 1-atom phosphoamide linkage.

Subunit B in FIG. 1 is designed for 6-atom repeating-unit backbones, as shown at B—B, in FIG. 2. In structure B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures.

Subunits C–E in FIG. 1 are designed for 7-atom unit-length backbones as shown for C—C through E—E in FIG. 2. In Structure C, the X moiety is as in Structure B and the moiety Y may be a methylene, sulfur, or preferably oxygen. In Structure D the X and Y moieties are as in Structure B. In Structure E, X is as in Structure B and Y is O, S, or NR.

In all subunits depicted in FIGS. 1A–E, Z is O or S, and $P_i$ or $P_j$ is adenine, cytosine, guanine or uracil.

A preferred "morpholino" oligonucleotide is composed of morpholino subunit structures of the form shown in FIGS. 2B-B, where (i) the structures are linked together by phosphorodiamidate containing linkages, one to three atoms long, joining the morpholino nitrogen of one subunit to the 5' exocyclic carbon of an adjacent subunit, (ii) $P_i$ and $P_j$ are purine or pyrimidine base-pairing moieties effective to bind, by base-specific hydrogen bonding, to a base in a polynucleotide, and $X=NH_2$, $Y=O$, and $Z=O$.

As noted above, the compound has a sequence which spans the start codon of a c-myc mRNA, meaning the compound contains a sequence complementary to a region of c-myc RNA containing the AUG mRNA start site and adjacent 5' and 3' base(s). The region of the mRNA against which the compound is directed is also referred to herein as the target sequence. The c-myc mRNA to which the antisense binds may be preprocessed (prespliced) mRNA, in which case the antisense compound may act to interfere with correct splicing, leading to truncated forms of the translated protein, or may bind to the processed mRNA, leading to inhibition of translation.

The compound is designed to hybridize to c-myc mRNA, under physiological conditions with a Tm substantially greater than 37° C., e.g., at least 50° C. and preferably 60° C.–80° C. Although the compound is not necessarily 100% complementary to the target sequence, it is effective to stably and specifically bind to the target sequence such that expression of the target sequence, is modulated. The appropriate length of the oligomer to allow stable, effective binding combined with good specificity is about 8 to 40 nucleotide base units, and preferably about 12–25 base units. Mismatches, if present, are less destabilizing toward the end regions of the hybrid duplex than in the middle. Oligomer bases that allow degenerate base pairing with target bases are also contemplated, assuming base-pair specificity with the target is maintained. The compound preferably contains internal 3-base triplet complementary to the AUG site, and bases complementary to one or more bases 5' and 3' to the start site. One preferred compound sequence is the 20mer identified as SEQ ID NO:1 and having the base sequence: 5'-ACG TTG AGG GGC ATC GTC GC-3', where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions.

The solubility of the antisense compound, and the ability of the compound to resist precipitation on storage in solution, can be further enhanced by derivatizing the oligomer with a solubilizing moiety, such as a hydrophilic oligomer, or a charged moiety, such as a charged amino acid or organic acid. The moiety can be chemically attached to the antisense compound, e.g., at its 5' end, by well-known derivatization methods. One preferred moiety is a defined length oligo ethylene glycol moiety, such as triethyleneglycol, coupled covalently to the 5' end of the antisense compound through a carbonate linkage, via a piperazine linking group forming a carbamate linkage with triethyleneglycol, where the second piperazine nitrogen is coupled to the 5'-end phosphorodiamidate linkage of the antisense. Alternatively, or in addition, the compound may be designed to include one a small number of charged backbone linkages, such as a phosphodiester linkage, preferably near one of the ends of the compound. The added moiety is preferably effective to enhance solubility of the compound to at least about 30.mgs/ml, preferably at least 50 mgs/ml in aqueous medium.

The effectiveness of a particular c-myc antisense sequence may be determined by known screening methods. For example, the oligomer is incubated with a cell culture expressing the target RNA, and the presence or absence of the heteroduplex is determined by techniques such as those set forth in below, or by monitoring the presence or absence of the encoded, full-length protein as determined by standard techniques such as ELISA or Western blotting, or the presence or absence of active protein.

In another embodiment, the antisense compound forms part of a particle composition for use in restenosis treatment. One such particle is a biodegradable particle, e.g., a polylactate or polyglycolic particle, containing entrapped antisense compound. The particles are preferably in the 1–5 micron range, and are useful for delivery by direct particle delivery to an angioplasty vessel site, as described below, either by being impressed into the vessel walls by pressure from a balloon against the wall, or by release from a particle carrier, such as a stent.

Alternatively, the particles can be microbubbles containing the compound in entrapped form. The preparation of suitable microbubbles as antisense carrier is described, for example, by Porter et all cited above. The particles may be delivered directly to the vessel site, that is, by contacting the vessel walls with a directly with a suspension of the particles, with compound release from the particles when the vessel region is exposed to ultrasonic energy.

In still another embodiment the particles are liposomes containing entrapped antisense compound. Because the liposome particles are applied directly to the vessel site, the liposomes may be conventional liposomes without surface modifications needed for achieving long circulation times.

III. Method of Treating Restenosis

Restenosis refers to the renarrowing of the vascular lumen following vascular intervention, such as coronary artery balloon angioplasty with or without stent insertion. It is clinically defined as greater than 50% loss of initial luminal diameter gain following the procedure. Restenosis is believed to occur in about 30% to 60% of lesions treated by angioplasty and about 20% of lesions treated with stents within 3 to 6 months following the procedure. (See, e.g., Dev).

"Restenosis" can also occur after a coronary artery bypass operation, wherein heart surgery is done to reroute, or "bypass," blood around clogged arteries and improve the supply of blood and oxygen to the heart. In such cases, the stenosis may occur in the transplanted blood vessel segments, and particularly at the junction of replaced vessels.

The present invention is directed to methods for reducing the risk (incidence) or severity (extent of stenosis), particularly following balloon angioplasty, or in response to other vessel trauma, such as following an arterial bypass operation. The method includes administering to the patient, the above-described antisense compound or composition, in an amount and via direct local administration of the compound at the vessel site of injury, to reduce the risk and/or severity of restenosis. In general, an amount of compound delivered to the vessel site between about 0.5–2 mg antisense compound is preferred, assuming substantially complete tissue uptake. Thus, where uptake into the vessel tissue is 10% of amount delivered, the amount delivered is preferably between 5 and 20 mg, preferably in a total volume of between about 0.2 to 1 ml.

In accordance with one aspect of the method, the modes of administration discussed below exploits one of more of the key features: (i) use of an antisense compound that has a high rate of cell uptake, (ii) the ability of the antisense compound to interfere with c-myc mRNA processing and mRNA translation, and (iii) local delivery of the compound by a mode of administration effective to achieve high localized concentration of the compound at the vessel injury site. The first two features have been discussed above. Modes of administration effective to achieve the third feature will now be detailed.

A. Iontophoresis

In one embodiment, the invention provides delivery of the antisense compound contacting the treated region with a reservoir containing an antisense compound and introducing the compound from the reservoir into the vessel by iontophoresis.

The antisense compounds described herein are uncharged. Optimal iontophoresis requires that the agent being administered have an overall net charge. The antisense compounds may be modified, as described above, to impart at least group that is charged at physiological or near-physiological pH. Alternatively, a pulsed electric field may be effective to facilitate the entry of uncharged antisense compounds into cells through an electroporesis effect.

Devices for use in carrying out iontophoretic drug delivery at a vessel site, e.g., by a balloon-catheter device have been described. In general, such devices include a reservoir for compound solution contained in a outer shell of the catheter's distal-tip balloon, an outer-balloon membrane allowing passage of the compound from the reservoir to the vessel wall, and an electrode communicating with the internal reservoir. A second counter-electrode is placed on the body, and a pulsed voltage is applied across the two electrodes to create a field that operates to draw charged compounds into vessel site. Devices, and electric pulse voltages and times follow those disclosed in the art, e.g., Fernandex-Ortiz, Dev, Robinson, and U.S. Pat. Nos. 5,593,974, 5,628,730, and 5,425,703).

Alternatively, a pulsed-field device designed for diffusion or injection of uncharged compound into the site, with cell uptake facilitated by pulsed-field induced electroporation is also contemplated.

Both methods provide the advantages of high-efficiency delivery of antisense compound into the vessel-wall cells, without the need for high fluid pressure in introducing the compound into the vessel tissue. Assuming a desired dose of 1 mg for delivery to the vessel site, and an efficiency of tissue uptake of between 25–80%, the total amount of compound contained in the reservoir for delivery is between about 1.25 and 4 mg, preferably at a concentration of between about 25–50 mgs/ml.

B. Nipple Balloon Catheter or Infiltrator

In a second general compound-delivery approach, the compound is injected into the vessel, that it, below the vessel surface, by means of an injection balloon catheter, such has been described (e.g., Roy, Pavlides, and Barath). The catheter, which is known commercially as an "Infiltrator Angioplasty Balloon Catheter" or "IABC", is a balloon catheter with 3 lumens: one for inflating the balloon, one central for a guidewire, and a third for drug delivery. On the surface of the balloon there are several longitudinal strips or channels, each having a plurality of injection needles, e.g., six needles, which upon inflation stand project above the channel surface and are connected to the drug-delivery lumen. When the balloon inflates, the needles penetrate the lesion, allowing drug delivery into the tunica media of the vessel wall.

In the present invention, the reservoir is filled with an antisense composition preferably containing a compound concentration of about 25–50 mgs/ml. Assuming an uptake into tissue of between about 15–50 percent, the amount of material injected is in the range of about 0.04 ml to 0.25 ml. The relatively small volume of compound that is administered reduced the risk of further injury by fluid injection under pressure into the injury site.

This mode of administration provides the advantage of high efficiency of uptake of the compound into the vessel tissue (20% or greater).

C. Hydrogel Coating

In a third delivery approach, the compound is embedded or dissolved in a diffusable medium, typically hydrogel, that coats the outer surface of a balloon, e.g., on a balloon catheter used for angioplasty. Methods for making and using such hydrogel coating on a catheter balloon have been described (e.g., Imanishi, Dick).

The hydrogel coating is formulated to include the antisense compound, at a preferred concentration of about 25–50 mgs/ml, and to release the selected dose of the compound for a period of about 5–60 minutes. The total amount of hydrogel is preferably between about 0.1 to 0.5 ml, allowing a total delivery of about 2.5 to 25 mgs, to accommodate an efficiency of tissue uptake of about 5–40%.

The hydrogel diffusion method may be combined with iontophoresis or electroporation, as described above, to enhance uptake of the compound from the gel into the tissue. In this case, the amount of material in the gel may be reduced substantially, in view of the enhanced efficiency of uptake.

The method has the advantages of maintaining intimate contact between the compound reservoir and vessel wall during the compound delivery period, allowing a relatively slow rate of drug release and uptake by cells, and avoiding elevated injection pressures.

D. Stents

This approach is similar to the hydrogel method above, except that the compound is contained in diffusable form in a coating contained on an intravascular stent. The stent may be placed at the vessel site at the time of balloon angioplasty, or placed at the site during coronary bypass surgery. Stent designs and materials, including biodegradable stents which release compound upon biodegradation, or which include a coating containing the compound in diffusable form, are known (Raman and U.S. Pat. Nos. 5,997,468 and 5,871,535).

As above, the stent or stent coating contains an amount of drug sufficient to deliver an approximately 0.5–2 mg dose over a 5–60 minute period, with an expected efficiency of uptake into tissue between 5–20 percent.

An implanted stent provides two advantages in practicing the present invention. First, it allows short term dosing, as with the other methods, and also continued dosing at a lower level over an extended period, e.g., 1–14 days, to block the early events of restenosis. Secondly, the stent itself may be effective in reducing the risk of restenosis, as has been reported.

E. Microparticles

Microparticles, such as polystyrene microparticles (Seradyn, Indianapolis, Ind.), biodegradable particles, liposomes or microbubbles containing the antisense compound in releasable form may be used for direct delivery of the compound into the vessel tissue.

The particles are prepared to contain a total dose of preferably 0.5–2 mg, with the total does depending on the efficiency of tissue uptake. Where the particles are injected into the tissue, this uptake will be high, e.g., 30–70% or higher. Where the particles are merely brought into contact with the vessel wall, the uptake of compound will be lower.

Methods for delivery the particles include injection of a particle suspension, or physical pressing the particles against the vessel wall, e.g., by balloon pressure in a balloon containing a outer coating of particles, e.g., in a hydrogel medium, or by embedding the particles in releasable form in a stent. Where the particles are microbubbles, the method additional includes exposing the administered particles to ultrasonic energy to explode the bubbles and release the bubbles at the particle sites. Particle delivery of the compound has the advantage of high uptake, particular where the particles are injected, and the potential for both high, short-term drug release and extended release from depot-release particles, e.g., biodegradable particles. The particles may also be coated with a binding agent, e.g., antibodies specific against growth factors or other proteins that are actively synthesized by endothelial cells during early cellular events leading to restenosis (see Bauriedel), to enhance the efficiency of compound uptake. Finally, the antisense compound may be selectively released from the particles at a desired time, as in the case for microbubbles.

IV. Restenosis Method

In a related aspect, the invention includes of treating the risk of restenosis in a region of a patient's coronary vessel. The method is carried out by administering to the patient, by local delivery directly into the region of injury, a morpholino antisense compound having (i) the base sequence identified as SEQ ID NO:1, (ii) a phosphorodiamidate backbone shown in. FIGS. 2B-B, where X=NH$_2$, Y=O, and Z=O, and (iii) a moiety that enhances the solubility of the compound, preferably to a solubility in aqueous medium of between 25–50 mgs/ml or greater. The administration is by direct contact With the vessel, using methods described above, or alternative methods, such as direct injection of the material through a Wilinsky type balloon catheter having a drug-solution reservoir, and means for injecting the solution through pores in the balloon against the vessel walls. The amount of material injected is preferably designed to provide a dose of material taken up by the tissue of between 0.5 to 2 mg antisense compound.

The moiety that increases compound solubility may be any biocompatible hydrophilic or charged moiety that can be coupled to the antisense compound, and which does not interfere with compound binding to the target sequence. One preferred moiety is a triethyleneglycol moiety derivatized to the antisense compound through a carbamate-piperizine linkage as described above.

V. Method of Assaying Effectiveness of Antisense Delivery and Uptake.

A standard indicator of the success of PTCA is one or more follow-up angiograms to determine the minimal lumen diameter of the affected vessel, that is, the extent of reocclusion. In determining the success of the methods of the present invention, follow-up angiograms may be completed one or more times following implantation of the c-myc antisense-containing catheter. Indicators of successful therapeutic intervention include a low percent occurrence of re-occlusion and/or restenosis and a prolonged time to occurrence of re-occlusion and/or restenosis.

In accordance with another aspect of the present invention, there is provided a rapid, easily performed method for confirming the presence of c-myc antisense compound in target cells, following antisense administration at the vessel site, and for comparing uptake levels of the compound achieved by various methods of compound administration to optimize conditions and dosages for effective restenosis treatment.

The method is based on the discovery, disclosed in above-cited U.S. provisional application 60/117,846 for "Non-Invasive Method for Detecting RNA", that a morpholino antisense compound of the type disclosed herein, when administered in vivo, can be detected in the urine of the receiving subject in a heteroduplex form consisting of the antisense compound and its RNA complement. The data indicate a sequence of events that include (i) uptake of the antisense compound by cells in the subject, (ii) binding of the compound intracellularly with the target mRNA, (iii) intracellular nuclease cleavage of single-stranded portions of the antisense/target complex, leaving a heteroduplex consisting of the antisense and its mRNA complement; (iv) secretion of the heteroduplex, presumably recognized as foreign molecules, by the cells, and (v) appearance of the heteroduplex in the blood and eventually the urine.

In the present case, this sequence of events allows for one to administer c-myc antisense, in accordance with any of the methods detailed above, and follow the uptake of the compound into target cells, by monitoring the presence and or quantity of c-myc antisense/mRNA in the urine or other body fluid, e.g., blood or serum.

In practicing the method, the antisense compound of the invention is administered to a patient or in an animal model in a selected dose, and by a selected mode of delivery, including any of the ones mentioned above. Thereafter, and at selected times after administration, e.g., 4, 12, and 24 hours post administration, the urine is monitored for the appearance and/or amount of heteroduplex to determine the effectiveness of compound uptake at the selected dose and method of administration.

In one exemplary assay format for use in urine detection, a sample containing an antisense/:RNA heteroduplex is reacted with a compound that specifically binds to or modifies the oligomer:RNA heteroduplex (e.g., a monoclonal antibody (mAb) specific for the particular heteroduplex) followed by detection of the modified or conjugated oligomer:RNA heteroduplex.

In another exemplary assay format, an antisense oligomer is modified by conjugating it with a reporter molecule before administration to the subject, followed by separation of heteroduplexes from uncomplexed reporter labeled antisense oligomer and detection of the heteroduplex-associated reporter molecule. In some cases such separation may be carried out by via chromatography or electrophoresis.

Exemplary detection methods include spectrophotometric detection (e.g., with a fluorescence detector), or detection using antibodies (e.g., FACS analysis). Such methods may be combined with separation methods in order to expedite analysis, e.g. chromatographic separation with simultaneous fluorescence detection or electrophoretic separation with detection by staining of gels, fluorescence or autoradiographic detection. Such techniques are known to those of skill in the art and readily adaptable to a given antisense oligomer and target RNA sequence.

Any fluorescent molecule known in the art for labeling nucleic acids may be used in the methods of the invention, for example, fluorescein and fluorescein derivatives such as carboxy fluorescein, 5-(4,6-dichlorotriazin-2-yl) amino fluorescein (5-DTAF); eosin; rhodamines such as Texas Red and tetramethylrhodamine; cyanine dyes such as thiazole orange, oxazole yellow and related dyes described in U.S. Pat. Nos. 4,957,870 and 4,888,867; pyrene; porphyrin dyes such as La JollaBlue. The fluorescent label should be selected such that its fluorescent lifetime is comparable in magnitude to the correlation time being measured, taking into account that temperature, viscosity, and the size of the oligonucleotide to which the fluorescent dye is conjugated all affect tumbling time. The fluorescent label is covalently linked or conjugated to the signal primer so as not to interfere with either emission of fluorescence from the label or hybridization of the probe to the target sequence. [See, also, U.S. Pat. Nos. 5,614,617 and 5,652,099.]

In other cases, antisense oligomers can be synthesized having a sequence complementary to a given target with the 5' end of the sequence attached to a reactive amino group as described by Smith, L. M., et al. Nuc. Acids Res. 13(7):2399 (1985). In such cases, biotin, peptide or an enzyme, e.g., alkaline phosphatase may be attached to the 5' amino group. [See, also U.S. Pat. No. 5,783,391.)

In still another embodiment, the heteroduplex can be detected, e.g., after isolation from the body-fluid sample, by mass spectroscopy. In studies conducted in support of the present invention, it was found that a heteroduplex of RNA:morpholino oligomer is readily resolved into two different-MW fractions (the two heteroduplex strands) by mass spectroscopy. This method thus provides a positive identification of the heteroduplex in terms of its two component strands.

As can be appreciated from above, the method allows one to readily assess the effectiveness of various modes, of administration, and optimal doses, typically doses that lead to maximal or near-maximal levels of heteroduplex in the urine. This will allow a physician to monitor the effectiveness of the treatment method and assure the physician that the antisense compound has been taken up by the vessel tissue. If, for example, the test shows low levels of heteroduplex after 24 hours, the physician might deem it necessary to retreat the site.

The following example illustrates the basic features of the assay method.

Example 1

In Vivo Studies with Antisense Oligomer:RNA Heteroduplexes

Calibration studies performed using an instrument capable of detecting fluorescein conjugated oligomers (Applied Biosystems Model 672 GeneScanner) were used to determine the migration rates of fluorescein-conjugated oligomers of various lengths; a 15-mer, a 20-mer, a 24-mer and a 38-mer ribozyme. Concentrations were evaluated in a GeneScanner.

Rats were injected with carboxyfluorescein-conjugated phosphorodiamidate morpholino oligomers (PMO) which is antisense to rat cytochrome P-4503A2.

Chromatograms of plasma samples prepared from blood withdrawn at the various times post-PMO administration showed the following. Plasma samples prepared from rats one hour post-injection contained fluorescent components which migrated at 270 and 340 minutes (two peaks due to the two possible carboxyfluorescein linkages which migrate differently). Plasma samples prepared from rats 24 hours post-injection contained fluorescent components which migrated at approximately 75 and 80 minutes. Mass spectral data (not shown) confirms that the shorter migration time is not due to degradation of the PMO and indicates that a PMO:RNA heteroduplex has been formed over that time.

Figure 3:
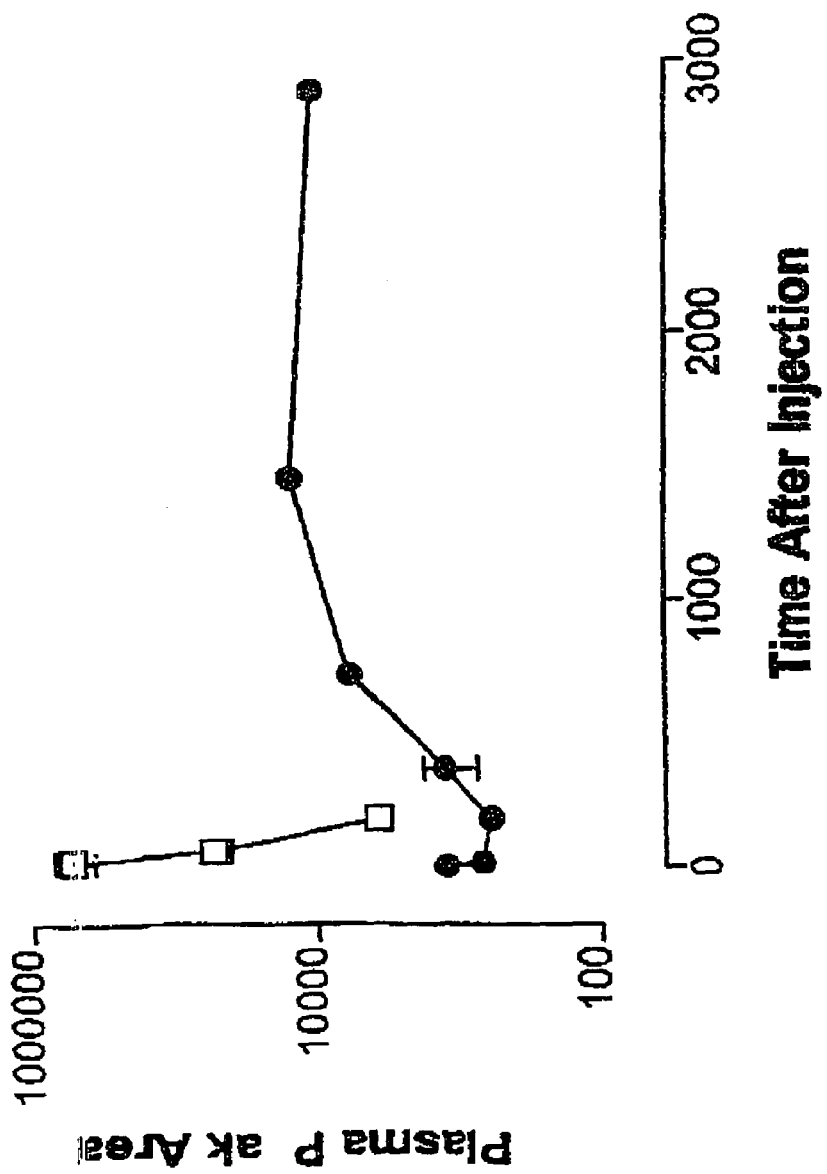
FIG. 3 is a kinetic representation of the disappearance of PMO monomer and appearance of RNA:PMO heterodimer in the plasma of rats administered the P450 antisense PMO.

FIG. 3 represents samples taken at various times (in minutes) post administration of the P450 antisense PMO, and indicates the disappearance of the PMO monomer (open squares) and the corresponding appearance of RNA:PMO heterodimer (solid circles) in the plasma of rats following such administration. Appearance of significant quantities of the duplex in plasma does not occur until the majority of the unduplexed PMO leaves the plasma in what is generally referred to as the "distribution phase". The PMO heteroduplex does not accumulate in plasma until after PMO monomer has distributed into the tissues of the subject where the complementary mRNA transcripts are localized. The charged RNA:PMO duplex presumably forms in these tissues and effluxes out of cells and back into plasma. This overall process requires several hours.

After administration of the p450 antisense PMO, fluorescein was detected in both the kidney and liver. Chromatograms of kidney tissue sample shows a band at 350 minutes consistent with unduplexed PMO and an additional band at 80 minutes consistent with the PMO:RNA heteroduplex, indicating both duplex and parent PMO which may reside in interstitial spaces or within the cells of the kidney. The liver tissue sample shows essentially no unduplexed PMO and significantly more PMO:RNA heteroduplex. These results are consistent with the observation that levels of P450 mRNA transcript are much lower in kidney than in liver.

Studies reflecting the time course of urinary clearance of unduplexed antisense PMO oligomer and antisense PMO oligomer:RNA heteroduplexes indicate that several hours are required for formation and efflux of PMO:RNA heteroduplex from tissues into plasma, followed by their ultimate appearance in urine.

Although the invention has been described with reference to specific methods and embodiments, it will be appreciated that various modifications and changes may be made without departing from the invention.

The invention claimed is:

1. A method for treating a vascular injury site in a human patient by reducing restenosis at the site, said method comprising:

administering to the patient, by intravascular delivery directly to the vascular injury site, a morpholino antisense compound having uncharged phosphorodiamidate intersubunit linkages of the form:

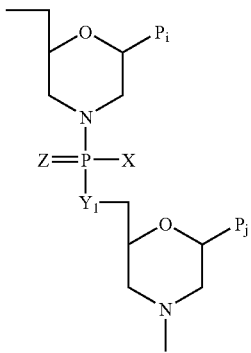

where X=$N(CH_3)_2$, Y=O, Z=O, and Pi and Pj are independently selected from adenine, guanine, cytosine, thymine and uracil; and comprising the sequence identified as SEQ ID NO:1, in an amount effective to reduce restenosis in the patient.

2. The method of claim 1, wherein said administering is carried out by injecting the antisense compound from an injection balloon catheter directly into the vascular injury site, under pressure, through injectors contained on the surface of the catheter balloon, wherein the vascular injury site comprises a vascular wall having a tunica media and wherein said injectors are capable of penetrating the tunica media in the vascular wall.

3. The method of claim 2, wherein the catheter balloon has a plurality of outer-facing channels that are connected to a drug-delivery lumen of the catheter, each channel having one or more injection ports, and said injecting includes forcing a solution or suspension of the antisense compound from said drug-delivery lumen through said injection ports when the balloon is in an inflated position.

4. The method of claim 3, wherein the amount of antisense compound administered is between 5 and 20 mg.

5. The method of claim 1, wherein said administering is carried out by contacting the vascular injury site with an intravascular stent having a coating containing the antisense compound in diffusible form.

6. The method of claim 5, wherein the coating is designed to release the majority of the antisense compound in the coating over a period of 5–60 minutes following balloon angioplasty.

7. The method of claim 6, wherein the intravascular stent is biodegradable.

8. A method for treating a vascular injury site in a human patient, said method comprising:

providing an intravascular stent wherein said stent or a coating on said stent contains a morpholino antisense compound in diffusible form, wherein the morpholino antisense compound has uncharged phosphorodiamidate intersubunit linkages of the form:

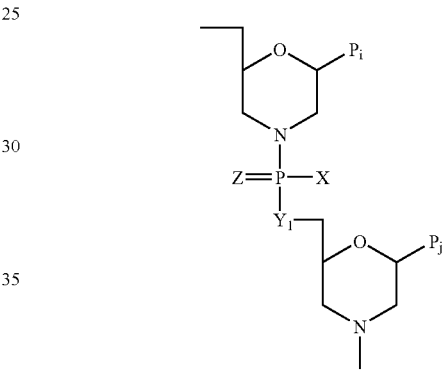

where X=$N(CH_3)_2$, Y=O, and Z=O, and Pi and Pj are independently selected from adenine, guanine, cytosine, thymine and uracil; and comprises the sequence identified as SEQ ID NO: 1, and contacting the vascular injury site with said stent, effective to administer said compound to the patient, in an amount effective to reduce restenosis in the patient.

9. The method of claim 8, wherein the coating is designed to release the majority of the antisense compound in the coating over a period of 5–60 minutes following balloon angioplasty.

10. The method of claim 8, wherein the stent is biodegradable.

11. The method of claim 8, wherein the compound is derivatized with a moiety that enhances the solubility of the compound in aqueous medium, to a level of at least about 30 mg/ml of the antisense compound.

12. The method of claim 11, wherein said moiety is triethyleneglycol attached to the 5' end of the compound.

13. The method of claim 8, wherein said contacting comprises placing the stent at the vessel site at the time of balloon angioplasty or during coronary bypass surgery.

* * * * *